(12) United States Patent
Zhao et al.

(10) Patent No.: US 11,172,681 B2
(45) Date of Patent: Nov. 16, 2021

(54) CRYSTALLINE FORM C OF SHUANGZUOCAOTONG, PREPARATION METHOD THEREFOR AND USE THEREOF

(71) Applicant: QINGDAO KINGAGROOT CHEMICAL COMPOUND CO., LTD., Shandong (CN)

(72) Inventors: De Zhao, Shandong (CN); Tao Jin, Shandong (CN); Beibei Lin, Shandong (CN); Qiang Ru, Shandong (CN)

(73) Assignee: Qingdao Kingagroot Chemical Compound Co., Ltd., Shandong (CN)

( * ) Notice: Subject to any disclaimer, the term of this patent is extended or adjusted under 35 U.S.C. 154(b) by 80 days.

(21) Appl. No.: 16/629,879

(22) PCT Filed: Jul. 15, 2017

(86) PCT No.: PCT/CN2017/093067
§ 371 (c)(1),
(2) Date: Jan. 9, 2020

(87) PCT Pub. No.: WO2019/010717
PCT Pub. Date: Jan. 17, 2019

(65) Prior Publication Data
US 2020/0178530 A1 Jun. 11, 2020

(30) Foreign Application Priority Data
Jul. 13, 2017 (CN) .......................... 201710567957.8

(51) Int. Cl.
*C07D 249/12* (2006.01)
*A01N 43/56* (2006.01)
*A01N 43/653* (2006.01)

(52) U.S. Cl.
CPC ......... *A01N 43/653* (2013.01); *C07D 249/12* (2013.01); *C07B 2200/13* (2013.01)

(58) Field of Classification Search
CPC ........................... A01N 43/56; C07B 2200/13
See application file for complete search history.

(56) References Cited

FOREIGN PATENT DOCUMENTS

| CN | 103980202 A | 8/2014 |
| CN | 105230629 A | 1/2016 |
| CN | 105503728 A | 4/2016 |
| CN | 105685049 A | 6/2016 |
| CN | 103980202 B | 1/2017 |
| CN | 105503728 B | 3/2017 |
| RU | 2577247 C2 | 3/2016 |

OTHER PUBLICATIONS

Caira, "Crystalline Polymorphism of Organic Compounds," Topics in Current Chemistry, vol. 198: Design of Organic Solids, Springer, Berlin, Heidelberg, p. 163-208 (1998).
Russian Patent Office, Office Action issued in Russian Application No. 2020106593/04(010226), dated Jul. 24, 2020.
Russian Patent Office, Search Report issued in Russian Application No. 2020106593/04(010226), dated Jul. 23, 2020.
International Bureau, International Search Report issued in Application No. PCT/CN2017/093067, dated Apr. 19, 2018.
Chinese Patent Office, First Office Action issued in Chinese Application No. 201710567957.8, dated Mar. 4, 2019.

*Primary Examiner* — Barbara P Badio
(74) *Attorney, Agent, or Firm* — Leydig, Voit & Mayer, Ltd.

(57) ABSTRACT

The present invention relates to the technical field of herbicide crystallization process, particularly to Crystalline form C of shuangzuocaotong, and a preparation method therefor and use thereof. The Crystalline form C of shuangzuocaotong has an X-ray powder diffraction pattern having characteristic absorption peaks at the following 2θ positions: 10.159, 10.658, 13.318, 14.579, 16.096, 18.061, 19.322, 19.68, 20.04, 20.659, 21.281, 23, 24.16, 24.619, 26.101, 26.74, 30.359, 31.018, 32.378, 35.398 and 38.26 degrees, wherein 2θ has an error range within ±0.2°. The Crystalline form C of shuangzuocaotong has good stability, and its compounded composition with additional active ingredient(s) has a good control effect to broadleaf weeds and some gramineous weeds in wheat, significantly better than that of Crystalline form A of shuangzuocaotong.

12 Claims, 1 Drawing Sheet

CRYSTALLINE FORM C OF SHUANGZUOCAOTONG, PREPARATION METHOD THEREFOR AND USE THEREOF

CROSS-REFERENCE TO RELATED APPLICATIONS

This patent application is the U.S. National Stage of International Patent Application No. PCT/CN2017/093067, filed Jul. 15, 2017, which claims the benefit of Chinese Patent Application No. 201710567957.8, filed Jul. 13, 2017, which are each incorporated by reference.

TECHNICAL FIELD

The present invention relates to technical field of herbicide crystallization process, particularly to Crystalline form C of shuangzuocaotong, and a preparation method therefor and use thereof.

BACKGROUND

Shuangzuocaotong has a chemical name of 1,3-Dimethyl-1H-pyrazole-4-carboxylic acid 4-[2-methanesulfonyl-4-trifluoromethyl-benzoyl]-1,3-dimethyl-1H-pyrazol-5-yl ester.

The structural formula of shuangzuocaotong is as the following:

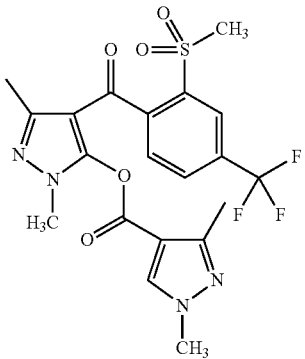 [SMILES: Cc1nn(C)cc1C(=O)Oc1c(C(=O)c2ccc(C(F)(F)F)cc2S(C)(=O)=O)c(C)nn1C]

Shuangzuocaotong is a new developed HPPD-inhibiting herbicide with excellent bioactivity for post-emergence stem and leaf treatment in wheat field, and can effectively control many malignant weeds in wheat. Patent for the compound has been granted and the number of announcement of grant of patent right is CN 103980202 B.

Polymorphism refers to a phenomenon in which a solid material exists in two or more different spatial arrangements to form solid states with different physicochemical properties. In the field of drug research, polymorphs include multi-component crystalline forms such as organic solvates, hydrates, and the like. Drug polymorphism is widespread in drug development and is an inherent property of organic small molecule compounds. Theoretically, small molecule drugs may have unlimited crystal packing modes, i.e. polymorphisms. The polymorphism phenomenon is not only regulated by internal factors, such as the spatial structure of the molecule itself and the performance of functional groups, and the intra-molecular and inter-molecular interactions, but also influenced by various factors like process design of drug synthesis, condition of crystallization and purification, selection of formulation adjuvant, formulation process route and granulating method, as well as the storage condition, package material, etc. Different crystalline forms are different in color, melting point, solubility, dissolution performance, chemical stability, reactivity, mechanical stability, etc. All these physicochemical properties or processability may directly influence the safety and effectiveness of drugs. Hence the research and control of crystalline form has become an important part in the process of drug development.

Currently, there is no report on crystalline forms of shaungzuocaotong, which is a new herbicide, in various literatures and patents. It was found that the synthesized technical material of shuangzuocaotong is in the form of Crystalline form A.

SUMMARY

The present invention provides Crystalline form C of a new herbicide, shuangzuocaotong, and a preparation method therefor and use thereof. With good stability and high weed control efficacy, the Crystalline form C of shuangzuocaotong is available for post-emergence weed control in wheat.

In the technical solution of the present invention, shuangzuocaotong was prepared by the following method described in CN 103980202 B. 2.5 g (0.022 mol) of 1,3-dimethyl-5-hydroxy pyrazole and 30 ml of methyl benzene were added in a three-neck flask, then 9.0 g (0.09 mol) of triethylamine was added under stirring. The temperature was controlled at 5-10° C. by ice bath. The methylbenzene solution of 6.3 g (0.022 mol) of 2-methylsulfonyl-4-trifluoromethyl benzoyl chloride was dropwise added and the reaction temperature was controlled not higher than 15° C. After the addition was completed, the ice-water bath was removed, the mixture was stirred at room temperature and left to react for 30 min. The reaction was monitored by TLC (ethyl acetate:petroleum ether=4:1, GF254, UV visualization). After the reaction finished, 0.2 g of 2-methyl-2-hydroxy propionitrile was added and the mixture was slowly heated to 45-50° C. under stirring. TLC (ethyl acetate:petroleum ether=2:1, GF254, UV visualization) was used to monitor the reaction. After the completeness of reaction, 9.0 g (0.023 mol) of N-ethylsulfonyl-N-(4-trifluoromethoxy phenyl) acetbromamide was added and the temperature was controlled at 60-65° C. to react for 8 hours. The mixture was cooled after the reaction was completed, added with 50 ml of water, and stirred evenly. The organic layer was extracted separately and washed with aqueous saturated NaCl solution. The solvent was removed and recovered and the residues were separated by column chromatography. 7.1 g of target product was obtained with a yield of 48.1%. $^1$HNMR (CDCl$_3$, 300 MHz): δ1.441 (t, 3H), 1.961 (s, 3H), 3.292 (s, 3H), 3.622 (q, 2H), 3.737 (s, 3H), 4.612 (s, 2H), 7.310 (d, 2H), 7.359 (d, 2H), 7.549 (d, 1H), 7.946 (d, 1H), 8.303 (s, 1H).

The synthetic methods in Example 1-Example 5 were taken as reference for Example 6-Example 60. The reactant was replaced by the corresponding pyrazole compounds and corresponding acyl chloride or halide for reaction to obtain the compounds of Formula (I) numbered from 006 to 060 as shown in Table 1. The test data of compounds numbered from 006 to 060 were listed in Table 1. Shuangzuocaotong in the present invention is the compound in Example 21.

Shuangzuocaotong obtained by preparation was in the form of Crystalline form A and on the basis of it, the Crystalline form C was further studied.

The present invention provides Crystalline form C of shuangzuocaotong, which has an X-ray powder diffraction pattern having characteristic absorption peaks at the following 2θ positions: 10.159, 10.658, 13.318, 14.579, 16.096, 18.061, 19.322, 19.68, 20.04, 20.659, 21.281, 23, 24.16, 24.619, 26.101, 26.74, 30.359, 31.018, 32.378, 35.398 and 38.26 degrees, wherein the he 2θ has an error range within ±0.2°. The characteristic absorption peaks have the following $I/I_0$ values: 22, 22.9, 18.9, 28.7, 100, 21.5, 17.6, 35, 10.7, 18.3, 11.1, 55.4, 61.3, 28.1, 12.2, 7.6, 10.1, 6.1, 9.4, 8.2, 7.6, respectively.

Preferably, the X-ray powder diffraction pattern is basically the same as shown in FIG. 2.

The present invention provides a method for preparing the Crystalline form C of shuangzuocaotong which comprises the following steps: shuangzuocaotong is dissolved in a solvent which is selected from a group consisting of: absolute ethyl alcohol, n-propyl alcohol, isobutyl alcohol, absolute ethyl ether, methyl tertiary butyl ether, butyl acetate, methyl benzene and isopropyl benzene, and then heated to complete dissolution; the solvent is removed by natural volatilization, and the Crystalline form C is obtained.

The present invention provides a herbicidal compounded composition which comprises the Crystalline form C of shuangzuocaotong and an adjuvant.

Preferably, the adjuvant is one or more selected from a group consisting of: solvents, solid diluents, emulsifiers, humectants, dispersants, antifreezes, defoamers and thickeners.

The solvents include but are not limited to the following: polar solvents such as water, N,N-dimethylformamide, dimethyl sulfoxide, N-alkyl pyrrolidone, methyl alcohol, ethyl alcohol, ethylene glycol, isopropyl alcohol, ethylene glycol butyl ether, propylene glycol methyl ether, etc.; aromatic solvent oils such as methyl benzene, dimethyl benzene, No. 100 solvent oil, No. 150 solvent oil, No. 180 solvent oil, No. 200 solvent oil, etc.; vegetable oils such as castor oil, linseed oil, sesame oil, corn oil, peanut oil, cottonseed oil, soybean oil, rapeseed oil and the corresponding methyl-esterified vegetable oils thereof; ketones such as cyclopentanone, cyclohexanone, cyclooctanone, 2-heptanone, isophorone and 4-hydroxy-4-methyl-2-pentanone, etc.; acetate esters such as methyl acetate, ethyl acetate, propyl acetate, sec-butyl acetate, isopentyl acetate, hexyl acetate, heptyl acetate, octyl acetate, etc; others such as decyl amide, cyclohexanol, decyl alcohol, benzyl alcohol, tetrahydrofurfuryl alcohol, etc.

The solid diluents may be either water soluble or water insoluble. Water soluble solid diluents include but are not limited to salts, for example, alkali metal phosphate (sodium dihydrogen phosphate), alkaline-earth metal phosphate, sulfates of sodium, potassium, magnesium and zinc, sodium chloride and potassium chloride, sodium acetate, sodium carbonate and sodium benzoate, and sugars and sugar derivatives such as sorbitol, lactose, sucrose and mannitol, corn starch, etc. Water insoluble solid diluents include but are not limited to clay, calcium carbonate, diatomite, white carbon black, calcium silicate, bentonite, aluminium-magnesium silicate and kaolin, etc.

The humectants include but are not limited to alkyl sulfosuccinate, laurate, alkyl sulfate, phosphate, ethoxyl fluorinated alcohol, ethoxylated silicone, alkylphenol ethoxylate, benzene sulfonate, alkyl-substituted benzene sulfonate, alkyl α-alkene sulfonate, naphthalene sulfonate, alkyl-substituted naphthalene sulfonic acid alkali metal salt, naphthalene sulfonic acid alkali metal salt and alkyl-substituted condensation product of naphthalene sulfonic acid ester and formaldehyde, alcohol ethoxylate.

The dispersants include but are not limited to sodium salt, calcium salt and ammonium salt of lignosulfonic acid; sodium salt and ammonium salt of maleic anhydride copolymer; sodium salt of condensed phenolsulfonic acid; condensation product of naphthalene sulfonic acid ester and formaldehyde; phosphate dispersants, polycarboxylate dispersants, etc.

The thickeners include but are not limited to guar gum, pectin, xanthan gum, alginate, methylcellulose, hydroxyethyl cellulose, hydroxypropyl cellulose and carboxymethyl cellulose. Synthetic thickeners include the derivatives of the aforesaid thickeners, and polyvinyl alcohol, polyacrylamide, polyvinyl pyrrolidone, various polyethers and the copolymers thereof, as well as polyacrylic acids and salts thereof.

Other formulation ingredients, for example, dyes, defoamers, desiccants may also be used in the present invention. The ingredients aforesaid are well known to those skilled in the art.

The composition may also comprises additional active ingredient(s).

Suitable active ingredient(s) which may be combined with the Crystalline form C of shuangzuocaotong according to the invention is, for example, a known active compound as described in for example *World Herbicide New Product Technology Handbook*, China Agricultural Science and Farming Techniques Press, 2010.9 and in the literature cited therein, for example, selected from the following various substances mentioned (note: the compounds are either named by the "common name" in accordance with the International Organization for Standardization (ISO) or by the chemical names, if appropriate together with a customary code number): acetochlor, butachlor, alachlor, propisochlor, metolachlor, s-metolachlor, pretilachlor, propachlor, ethachlor, napropamide, R-left handed napropamide, propanil, mefenacet, diphenamid, diflufenican, ethaprochlor, beflubutamid, bromobutide, dimethenamid, dimethenamid-P, etobenzanid, flufenacet, thenylchlor, metazachlor, isoxaben, flamprop-M-methyl, flamprop-M-propyl, allidochlor, pethoxamid, chloranocryl, cyprazine, mefluidide, monalide, delachlor, prynachlor, terbuchlor, xylachlor, dimethachlor, cisanilide, trimexachlor, clomeprop, propyzamide, pentanochlor, carbetamide, benzoylprop-ethyl, cyprazole, butenachlor, tebutam, benzipram, mogrton, dichlofluanid, naproanilide, diethatyl-ethyl, naptalam, flufenacet, benzadox, chlorthiamid, chlorophthalimide, isocarbamide, picolinafen, atrazine, simazine, prometryn, cyanatryn, simetryn, ametryn, propazine, dipropetryn, SSH-108, terbutryn, terbuthylazine, triaziflam, cyprazine, proglinazine, trietazine, prometon, simetone, aziprotryne, desmetryn, dimethametryn, procyazine, mesoprazine, sebuthylazine, secbumeton, terbumeton, methoprotryne, cyanatryn, ipazine, chlorazine, atraton, pendimethalin, eglinazine, cyanuric acid, indaziflam, chlorsulfuron, metsulfuron-methyl, bensulfuron methyl, chlorimuron-ethyl, tribenuron-methyl, thifensulfuron-methyl, pyrazosulfuron-ethyl, mesosulfuron-methyl, iodosulfuron-methyl sodium, foramsulfuron, cinosulfuron, triasulfuron, sulfometuron methyl, nicosulfuron, ethametsulfuron-methyl, amidosulfuron, ethoxysulfuron, cyclosulfamuron, rimsulfuron, azimsulfuron, flazasulfuron, monosulfuron, monosulfuron-ester, flucarbazone-sodium, flupyrsulfuron-methyl, halosulfuron-methyl, oxasulfuron, imazosulfuron, primisulfuron, propoxycarbazone, prosulfuron, sulfosulfuron, trifloxysulfuron, triflusulfuron-methyl, tritosulfuron, sodium metsulfuron methyl, flucetosulfuron, HNPC-C, orthosulfamuron, propyrisulfuron, metazosulfuron, aciflurofen, fomesafen, lactofen, fluoroglycofen-ethyl, oxyfluorfen, chlomitrofen, aclonifen, ethoxyfen-ethyl, bifenox, nitrofluorfen, chlomethoxyfen, fluorodifen, fluoronitrofen, furyloxyfen, nitrofen, TOPE, DMNP, PPG1013, AKH-7088, halosafen, chlortoluron, isoproturon, linuron, diuron, dymron, fluometuron, benzthiazuron, methabenzthiazuron, cumyluron, ethidimuron, isouron, tebuthiuron, buturon, chlorbromuron, methyldymron, phenobenzuron, SK-85, metobromuron, metoxuron, afesin, monuron, siduron, fenuron, fluothiuron, neburon, chloroxuron, noruron, isonoruron, 3-cyclooctyl-1, thiazfluron, tebuthiuron, difenoxuron, parafluron, methylamine tribunil, karbutilate, trimeturon, dimefuron, monisouron, anisuron, methiuron, chloreturon, tetrafluron, phenmedipham, phenmedipham-ethyl, desmedipham, asulam, terbucarb, barban, propham, chlorpropham, rowmate, swep, chlorbufam, carboxazole, chlorprocarb, fenasulam, BCPC, CPPC, carbasulam, butylate, benthiocarb, vemolate, molinate, triallate, dimepiperate, esprocarb, pyributicarb, cycloate, avadex, EPTC, ethiolate, orbencarb, pebulate, prosulfocarb, tiocarbazil, CDEC, dimexano, isopolinate, methiobencarb, 2,4-D butyl ester, MCPA-Na, 2,4-D isooctyl ester, MCPA isooctyl ester, 2,4-D sodium salt, 2,4-D dimethyla mine salt, MCPA-thioethyl, MCPA, 2,4-D propionic acid, high 2,4-D propionic acid salt, 2,4-D butyric acid, MCPA propionic acid, MCPA propionic acid salt, MCPA butyric acid, 2,4,5-D, 2,4,5-D propionic acid, 2,4,5-D butyric acid, MCPA amine salt, dicamba, erbon, chlorfenac, saison, TBA, chloramben, methoxy-TBA, diclofop-methyl, fluazifop-butyl, fluazifop-P-butyl, haloxyfop-methyl, haloxyfop-P, quizalofop-ethyl, quizalofop-P-ethyl, fenoxaprop-ethy, fenoxaprop-P-ethyl, propaquizafop, cyhalofop-butyl, metamifop, clodinafop-propargyl, fenthiaprop-ethyl, chloroazifop-propynyl, poppenate-methyl, trifopsime, isoxapyrifop, paraquat, diquat, oryzalin, ethalfluralin, isopropalin, nitralin, profluralin, prodinamine, benfluralin, fluchloraline, dinitramina, dipropalin, chlomidine, methalpropalin, dinoprop, glyphosate, anilofos, glufosinate ammonium, amiprophos-methyl, sulphosate, piperophos, bialaphos-sodium, bensulide, butamifos, phocarb, 2,4-DEP, H-9201, zytron, imazapyr, imazethapyr, imazaquin, imazamox, imazamox ammonium salt, imazapic, imazamethabenz-methyl, fluroxypyr, fluroxypyr-mepthyl, clopyralid, picloram, trichlopyr, dithiopyr, haloxydine, 3,5,6-trichloro-2-pyridinol, thiazopyr, fluridone, aminopyralid, diflufenzopyr, triclopyr-butotyl, Cliodinate, sethoxydim, clethodim, cycloxydim, alloxydim, clefoxydim, butroxydim, tralkoxydim, tepraloxydim, buthidazole, metribuzin, hexazinone, metamitron, ethiozin, ametridione, amibuzin, bromoxynil, bromoxynil octanoate, ioxynil octanoate, ioxynil, dichlobenil, diphenatrile, pyraclonil, chloroxynil, iodobonil, flumetsulam, florasulam, penoxsulam, metosulam, cloransulam-methyl, diclosulam, pyroxsulam, benfuresate, bispyribac-sodium, pyribenzoxim, pyriftalid, pyriminobac-methyl, pyrithiobac-sodium, benzobicylon, mesotrione, sulcotrione, tembotrione, tefuryltrione, bicyclopyrone, ketodpiradox, isoxaflutole, clomazone, fenoxasulfone, methiozolin, fluazolate, pyraflufen-ethyl, pyrazolynate, difenzoquat, pyrazoxyfen, benzofenap, nipyraclofen, pyrasulfotole, topramezone, pyroxasulfone, cafenstrole, flupoxam, aminotriazole, amicarbazone, azafenidin, carfentrazone-ethyl, sulfentrazone, bencarbazone, benzfendizone, butafenacil, bromacil, isocil, lenacil, terbacil, flupropacil, cinidon-ethyl, flumiclorac-pentyl, flumioxazin, propyzamide, MK-129, flumezin, pentachlorophenol, dinoseb, dinoterb, dinoterb acetate, dinosam, DNOC, chloronitrophene, medinoterb acetate, dinofenate, oxadiargyl, oxadiazon, pentoxazone, Flufenacet, fluthiacet-methyl, fentrazamide, flufenpyr-ethyl, pyrazon, brompyrazon, metflurazon, kusakira, dimidazon, oxapyrazon, norflurazon, pyridafol, quinclorac, quinmerac, bentazone, pyridate, oxaziclomefone, benazolin, clomazone, cinmethylin, ZJ0702, pyribambenz-propyl, indanofan, sodium chlorate, dalapon, trichloroacetic acid, monochloroacetic acid, hexachloroacetone, flupropanate, cyperquat, bromofenoxim, epronaz, methazole, flurtamone, benfuresate, ethofumesate, tioclorim, chlorthal, fluorochloridone, tavron, acrolein, bentranil, tridiphane, chlorfenpropmethyl, thidiarizonaimin, phenisopham, busoxinone, methoxyphenone, saflufenacil, clacyfos, chloropon, alorac, diethamquat, etnipromid, iprymidam, ipfencarbazone, thiencarbazone-methyl, pyrimisulfan, chlorflurazole, tripropindan, sulglycapin, prosulfalin, cambendichlor, aminocyclopyrachlor, rodethanil, benoxacor, fenclorim, flurazole, fenchlorazole-ethyl, cloquintocet-mexyl, oxabetrinil, MG/91, cyometrinil, DKA-24, mefenpyr-diethyl, furilazole, fluxofenim, isoxadifen-ethyl, dichlormid, halauxifen-methyl, DOW 848, UBH-509, D489, LS 82-556, KPP-300, NC-324, NC-330, KH-218, DPX-N8189, SC-0744, DOWC0535, DK-8910, V-53482, PP-600, MBH-001, KIH-9201, ET-751, KIH-6127 and KIH-2023. It had been experimentally verified that the Crystalline form C of shuangzuocaotong according to the invention had obvious synergistic effect with one or more of the herbicides listed above.

Preferably, the additional active ingredient(s) includes, but is not limited to, MCPA-Na, MCPA-isooctyl ester, 2,4-D butyl ester, 2,4-D isooctyl ester, MCPA-dimethylamine salt, fluroxypyr, fluroxypyr-mepthyl, halauxifen-methyl, dicamba, isoproturon, chlorotoluron, diflufenican, picolinafen, carfentrazone-ethyl, fluoroglycofen-ethyl, fenoxaprop-P-ethyl, clodinafop-propargyl (acid), tralkoxydim, pinoxaden, halosulfuron-methyl, mesosulfuron-methyl, flucarbazone-sodium, florasulam, pyroxsulam, metribuzin, prometryn, terbutryn, bentazone, bromoxynil, bromoxynil octanoate, or flufenacet, etc.

The composition may have a total mass content of active ingredients within 75%, preferably within 50%.

The formulation of the said composition may be suspension concentrate (SC), oil dispersion (OD), emulsifiable concentrate (EC), microemulsion (ME), granule (GR), suspoemulsion (SE) or water-dispersible granule (WDG).

The Crystalline form C of shuangzuocaotong or the herbicidal compounded composition may be used in controlling broadleaf weeds or some gramineous weeds in wheat.

The Crystalline form C of shuangzuocaotong in the present invention is good in stability, and the Crystalline form C or the composition thereof with additional active ingredient(s) has good weed control effect to broadleaf weeds and some gramineous weeds in wheat, and the effect is obviously better than Crystalline form A.

SPECIFIC MODELS FOR CARRYING OUT THE INVENTION

Figure 1:
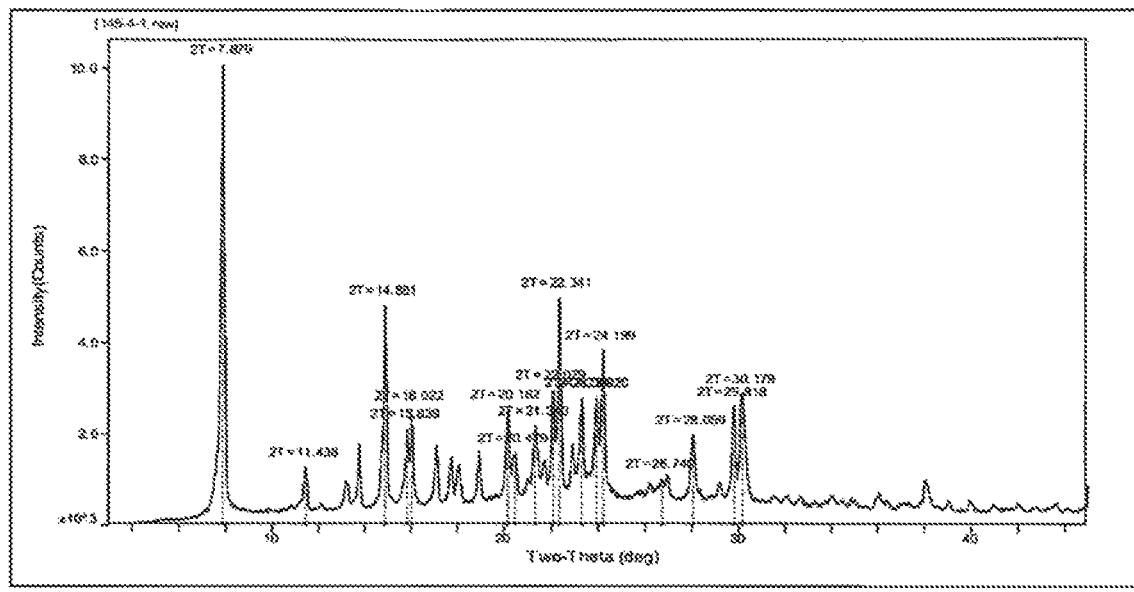
FIG. 1 is the XRPD pattern of Crystalline form A of shuangzuocaotong in Example 1 of the present invention.

The above contents of the present invention will be described in detail with reference to the following examples. However, it should not be understood that the scope of the above described subject of the present invention is limited to the following examples. All the techniques realized on the strength of the above described contents of the present invention is within the scope of the present invention.

Determination Method of XRPD

Instrument model: Bruker D8 advance, target: Cu Kα (40 kV, 40 mA), distance between sample and detector: 30 cm, scanned area 3°-45° (2θ value), scan path: 0.05 s

Example 1

The method in CN 103980202 B was taken as reference to obtain the technical material of shuangzuocaotong, which was in the form of Crystalline form A.

Example 2

3000 g of Crystalline form A of shuangzuocaotong technical material was placed into a 10 L flask. 6 L of absolute ethyl alcohol, n-propyl alcohol, isobutanol, absolute ethyl ether, methyl tert-butyl ether, butyl acetate, methyl benzene or isopropyl benzene was added. The materials were dissolved completely upon heating and stirring, and then was leaved for volatilizing naturally at or below 25° C. until the absolute ethyl alcohol, n-propyl alcohol, isobutanol, absolute ethyl ether, methyl tert-butyl ether, butyl acetate, methyl benzene or isopropyl benzene as volatilized completely to obtain the powder of Crystalline form C of shuangzuocaotong.

Physicochemical Stability Test

The Crystalline form A of shuangzuocaotong obtained from Example 1 and the Crystalline form C of shuangzuocaotong obtained from Example 2 were subjected to HPLC and the contents of Crystalline form A and Crystalline form C were about 96.0% by actual measurement. Thereafter, technical materials of the two crystalline forms were placed into ovens with temperatures of 25° C., 40° C., 55° C. and 70° C. respectively and left there for 2 months for thermal storage test. Then the type of crystalline form and the purity were determined and results were listed below in Table 1.

TABLE 1

Stability test of different crystalline forms of shuangzuocaotong

| Sample | Crystalline form A of shuangzuocaotong of Example 1 | | Crystalline form C of shuangzuocaotong of Example 2 | |
|---|---|---|---|---|
| | Crystalline form | Purity | Crystalline form | Purity |
| 25° C. | Crystalline form A | 96.0% | Crystalline form C | 96.0% |
| 40° C. | Crystalline form A | 95.5% | Crystalline form C | 95.8% |
| 55° C. | Crystalline form A | 95.1% | Crystalline form C | 95.7% |
| 70° C. | Crystalline form A | 94.2% | Crystalline form C | 95.2% |

It is shown in table 1 that both Crystalline forms A and C of shuangzuocaotong are in good stability at different temperatures. Particularly, even at the high temperature of 70° C., the crystalline forms maintain good physicochemical stability and the crystalline forms are unchanged. The purity of Crystalline form C is better than that of Crystalline form A, which indicates Crystalline form C is of high application potential.

Preparation Process and in-Door Bioassay Test

The Crystalline form A of shuangzuocaotong obtained from Example 1 and the Crystalline form C of shuangzuocaotong obtained from Example 2 were processed to preparations according to the following formulations. Detailed formulations are as the following:

5% Shuangzuocaotong OD

5% shuangzuocaotong+5% emulsifier calcium dodecyl benzene sulfonate+8% emulsifier phenethyl phenol polyoxyethylene ether+4% emulsifier castor oil polyoxyethylene ether+2.5% thickener organobentonite+2% thickener silicon dioxide by gas phase method+20% dispersion medium soybean oil+balance of dispersion medium methyl oleate.

8% Shuangzuocaotong SC

8% shuangzuocaotong+4% dispersant polycarboxylate+2% humenctant fatty alcohol polyoxyethylene ether+0.25% thickener xanthan gum+0.5% thickener carboxymethyl cellulose+5% antifreezer glycerol+0.1% defoamer silicone oil+balance of water 40% Shuangzuocaotong•MCPA-Na WP 5% shuangzuocaotong+35% MCPA-Na+6% polycarboxylates dispersant+5% fatty alcohol polyoxyethylene ether+5% white carbon black by precipitation method+balance of calcined kaolin 27% Shuangzuocaotong•MCPA-isooctyl Ester EW 2.5% shuangzuocaotong+24.5% MCPA-isooctyl ester+5% cyclohexanone+3% phenethyl phenol polyoxyethylene ether phosphate triethanolamine salt+2% phenethyl phenol polyoxyethylene ether+3% castol oil polyoxyethylene ether+3% ethylene glycol+balance of water 25% Shuangzuocaotong•2,4-D butyl Ester EC 2.5% shuangzuocaotong+22.5% 2,4-D butyl ester+10% isopropanol+4% calcium dodecyl benzene sulfonate+6% castol oil polyoxyethylene ether+balance of No. 150 aromatic solvent oil 27% Shuangzuocaotong•2,4-D Isooctyl Ester EC 2.5% shuangzuocaotong+24.5% 2,4-D isooctyl ester+5% cyclohexanone+4% calcium dodecylbenzene sulfonate+6% nonyl phenol polyoxyethylene ether+balance of No. 100 aromatic solvent oil 17% Shuangzuocaotong•Fluroxypyr ME 5% shuangzuocaotong+12% fluroxypyr+10% cyclohexanone+10% ethyl alcohol+8% sodium di-sec-octyl maleate sulfonate+8% phenethyl phenol polyoxyethylene ether+3% phenethyl phenol polyoxyethylene ether formaldehyde resin condensate+balance of water 3% Shuangzuocaotong•Halauxifen-methyl EW 2.5% shuangzuocaotong+0.5% halauxifen-methyl+10% cyclohexanone+10% No. 150 solvent oil+3% nonylphenol polyoxyethylene ether phosphate triethanolamine salt+2% phenethyl phenol polyoxyethylene ether+3% castor oil polyoxyethylene ether+3% ethylene glycol+balance of water 30% Shuangzuocaotong•Dicamba WP 5% shuangzuocaotong+25% dicamba+6% polycarboxylates dispersant+5% fatty alcohol polyoxyethylene ether+5% white carbon black by precipitation method+balance of calcined kaolin 20% Shuangzuocaotong•Bromoxynil EC 2.5% shuangzuocaotong+17.5% bromoxynil+5% phenethyl phenol polyoxyethylene ether phosphate triethanolamine salt+5% fatty acid polyoxyethylene ester+8% castor oil polyoxyethylene ether+2% organobentonite+balance of methyl oleate 27% Shuangzuocaotong•Bromoxynil Octanoate EC 2.5% shuangzuocaotong+24.5% bromoxynil octanoate+5% N-methyl pyrrolidone+4% calcium dodecylbenzene sulfonate+5% fatty alcohol polyoxyethylene ether+balance of No. 100 aromatic solvent oil 35% Shuangzuocaotong•Isoproturon SC 1.5% shuangzuocaotong+33.5% isoproturon+5% sodium lignin sulfonate+2% nekal+0.2% xanthan gum+5% glycerol+balance of water 50% Shuangzuocaotong•Terbutryn SC 2.5% shuangzuocaotong+47.5% terbutryn+5% naphthalene sulfonate+2% fatty alcohol polyoxyethylene ether+0.1% xanthan gum+5% glycerol+balance of water 35% Shuangzuocaotong•Diflufenican SC 5% shuangzuocaotong+30% diflufenican+5% nonylphenol polyoxyethylene ether phosphate triethanolamine salt+2% fatty alcohol polyoxyethylene ether+0.15% xanthan gum+5% glycerol+balance of water 40% Shuangzuocaotong•Picolinafen SC 25% shuangzuocaotong+15% picolinafen+5% polycarboxylates dispersant+2% nonylphenol polyoxyethylene ether+0.2% xanthan gum+5% glycerol+balance of water 12% Shuangzuocaotong•Flufenacet SC 2% shuangzuocaotong+10% flufenacet+5% polycarboxylates dispersant+2% nonylphenol polyoxyethylene ether+0.2% xanthan gum+5% glycerol+balance of water 22% Shuangzuocaotong•MCPA-Dimethylamine Salt SC 2.5% shuangzuocaotong+19.5% MCPA-dimethylamine salt+5% polycarboxylates dispersant+2% fatty alcohol polyoxyethylene ether+0.3% xanthan gum+5% glycerol+balance of water 50% Shuangzuocaotong•Chlortoluron WP 1.5% shuangzuocaotong+48.5% chlortoluron+10% sodium lignin sulfonate+5% nekal+5% white carbon black by precipitation method+balance of diatomite 33% Shuangzuocaotong•Prometryn WP 3% shuangzuocaotong+30% prometryn+8% naphthalene sulfonate+5% fatty alcohol polyoxyethylene ether+5% white carbon black by precipitation method+balance of calcined kaolin 3% Shuangzuocaotong•Carfentrazone-Ethyl WDG 2.5% shuangzuocaotong+0.5% carfentrazone-ethyl+10% naphthalene sulfonates+5% nekal+1% disintegrant polyvinyl alcohol+balance of filler diatomite 14% Shuangzuocaotong•Metribuzin WDG 2.5% shuangzuocaotong+11.5% metribuzin+10% polycarboxylates+5% polyethylene glycol+1% disintegrant polyvinyl alcohol+balance of filler diatomite 3% Shuangzuocaotong•Fluoroglycofen-Ethyl EC 2.5% shuangzuocaotong+0.5% fluoroglycofen-ethyl+5% cyclohexanone+5% calcium dodecyl benzene sulfonate+5% phenethyl phenol polyoxyethylene ether+balance of No. 100 aromatic solvent oil 9% Shuangzuocaotong•Fenoxaprop-P-Ethyl EW 2.5% shuangzuocaotong+6.5% fenoxaprop-P-ethyl+6% cyclohexanone+6% No. 150 solvent oil+10% ethyl alcohol+8% calcium dodecyl benzene sulfonate+8% nonyl phenol polyoxyethylene ether+5% phenethyl phenol polyoxyethylene ether formaldehyde resin condensate+balance of water 14% Shuangzuocaotong.Clodinafop-Propargyl EW 4% shuangzuocaotong+10% clodinafop-propargyl+10% cyclohexanone+10% ethylene glycol butyl ether+8% calcium dodecyl benzene sulfonate+8% castor oil polyoxyethylene ether+5% phenethyl phenol polyoxyethylene ether formaldehyde resin condensate+balance of water 17% Shuangzuocaotong•Pinoxaden EW 5% shuangzuocaotong+12% pinoxaden+10% cyclohexanone+5% No. 150 solvent oil+10% ethylene glycol butyl ether+8% calcium dodecyl benzene sulfonate+8% fatty alcohol polyoxyethylene ether+5% phenethyl phenol polyoxyethylene ether formaldehyde resin condensate+balance of water 65% Shuangzuocaotong•Tralkoxydim WDG 5% shuangzuocaotong+60% tralkoxydim+15% polycarboxylates+5% nekal+1% disintegrant polyvinyl alcohol+balance of filler bentonite 39% Shuangzuocaotong•Halosulfuron-Methyl WDG 15% shuangzuocaotong+24% halosulfuron-methyl+20% polycarboxylates+5% polyethylene glycol+1% disintegrant polyvinyl alcohol+balance of filler diatomite 7% Shuangzuocaotong•Mesosulfuron-Methyl OD 5.2% shuangzuocaotong+1.8% mesosulfuron-methyl+5% sodium di-sec-octyl maleate sulfonate+5% dehydrated sorbitol fatty acid polyoxyethylene ester+6% castor oil polyoxyethylene ether+3% organobentonite+3% white carbon black by gas phase method+20% soybean oil+balance of methyl oleate 11% Shuangzuocaotong•Flucarbazone-Sodium OD 5% shuangzuocaotong+6% flucarbazone-sodium+5% fatty alcohol polyoxyethylene ether phosphate triethanolamine salt+5% fatty alcohol polyoxyethylene ether+4% castor oil polyoxyethylene ether+3% organobentonite+20% soybean oil+balance of methyl oleate 6% Shuangzuocaotong•Florasulam OD 5% shuangzuocaotong+1% florasulam+5% sodium di-sec-octyl maleate sulfonate+5% dehydrated sorbitol fatty acid polyoxyethylene ester+4% nonylphenol polyoxyethylene ether+2.6% organobentonite+25% soybean oil+balance of methyl oleate 7% Shuangzuocaotong•Pyroxsulam OD 5% shuangzuocaotong+2% pyroxsulam+5% fatty alcohol polyoxyethylene ether phosphate triethanolamine salt+5% dehydrated sorbitol fatty acid polyoxyethylene ester+6% nonylphenol polyoxyethylene ether+3% organobentonite+25% soybean oil+balance of methyl oleate 38% Shuangzuocaotong•Bentazone OD 1.5% shuangzuocaotong+36.5% bentazone+5% sodium di-sec-octyl maleate sulfonate+5% nonylphenol polyoxyethylene ether+8% castor oil polyoxyethylene ether+0.5% organobentonite+balance of methyl oleate Determination using Greenhouse pot-cultured method: bamyardgrass (*Echinochloa crusgalli*) at 3-4 leaf stage (from the corn field of test site in Huangdao District, Shandong Province); Crickweed (*Malachium aquaticum*) at 3-5 leaf stage (seeds collected from Siyang county, Suqian city, Jiangsu Province); 3WP-2000 type travelling spray tower (Nanjing Research Institute for Agricultural Mechanization, Ministry of Agriculture) was used to conduct uniform stem and leaf spray with 4 replicates for each treatment, and the average plant control (visual) 30 days after the application (30 DAA) are as follows (see Table 2).

TABLE 2

Control effect (%) of preparations with different crystalline forms of shuangzuocaotong (30 DAA).

| Preparation | Application rate g/hm² | Barnyardgrass control effect % | Crickweed | Preparation | Application rate g/hm² | Barnyardgrass control effect % | Crickweed |
|---|---|---|---|---|---|---|---|
| 5% Crystalline form C of shuangzuocaotong OD | 15.0 | 77.3 | 87.4 | 5% Crystalline form A of shuangzuocaotong OD | 15.0 | 50.9 | 57.4 |

TABLE 2-continued

Control effect (%) of preparations with different crystalline forms of shuangzuocaotong (30 DAA).

| Preparation | Application rate g/hm² | Barnyard-grass control effect % | Crickweed effect % | Preparation | Application rate g/hm² | Barnyard-grass control effect % | Crickweed effect % |
|---|---|---|---|---|---|---|---|
| 8% Crystalline form C of shuangzuocaotong SC | 22.5 | 91.8 | 92.2 | 8% Crystalline form A of shuangzuocaotong SC | 22.5 | 43.8 | 51.4 |
| 40% Crystalline form C of shuangzuocaotong ·+ MCPA-Na WP | 90.0 | 82.5 | 94.7 | 40% Crystalline form A of shuangzuocaotong ·+ MCPA-Na WP | 90.0 | 50.4 | 68.5 |
| 27% Crystalline form C of shuangzuocaotong ·+ MCPA-isooctyl ester EW | 121.5 | 83.4 | 96.4 | 27% Crystalline form A of shuangzuocaotong + MCPA-isooctyl ester EW | 121.5 | 52.7 | 65.4 |
| 25% Crystalline form C of shuangzuocaotong ·+ 2,4-D butyl ester EC | 112.5 | 81.2 | 97.5 | 25% Crystalline form A of shuangzuocaotong ·+ 2,4-D butyl ester EC | 112.5 | 51.2 | 74.1 |
| 27% Crystalline form C of shuangzuocaotong ·+ 2,4-D-isooctyl ester EC | 121.5 | 82.5 | 97.2 | 27% Crystalline form A of shuangzuocaotong ·+ 2,4-D-isooctyl ester EC | 121.5 | 55.6 | 67.7 |
| 17% Crystalline form C of shuangzuocaotong ·+ fluroxypyr ME | 38.3 | 82.1 | 100.0 | 17% Crystalline form A of shuangzuocaotong ·+ fluroxypyr ME | 38.3 | 55.6 | 70.4 |
| 3% Crystalline form C of shuangzuocaotong ·+ halauxifen-methyl EW | 13.5 | 81.4 | 95.3 | 3% Crystalline form A of shuangzuocaotong ·+ halauxifen-methyl EW | 13.5 | 53.2 | 50.7 |
| 30% Crystalline form C of shuangzuocaotong + dicamba WP | 67.5 | 82.3 | 97.3 | 30% Crystalline form A of shuangzuocaotong ·+ dicamba WP | 67.5 | 57.4 | 61.7 |
| 20% Crystalline form C of shuangzuocaotong + bromoxynil EC | 90.0 | 83.2 | 100.0 | 20% Crystalline form A of shuangzuocaotong ·+ bromoxynil EC | 90.0 | 50.6 | 65.8 |
| 27% Crystalline form C of shuangzuocaotong ·+ bromoxynil octanoate EC | 121.5 | 81.2 | 100.0 | 27% Crystalline form A of shuangzuocaotong ·+ bromoxynil octanoate EC | 121.5 | 51.3 | 79.2 |
| 35% Crystalline form C of shuangzuocaotong ·+ isoproturon SC | 262.5 | 90.8 | 100.0 | 35% Crystalline form A of shuangzuocaotong ·+ isoproturon SC | 262.5 | 60.7 | 75.2 |
| 50% Crystalline form C of shuangzuocaotong ·+ terbutryn SC | 225.0 | 92.4 | 98.3 | 50% Crystalline form A of shuangzuocaotong ·+ terbutryn SC | 225.0 | 66.7 | 65.6 |
| 35% Crystalline form C of shuangzuocaotong ·+ diflufenican SC | 78.8 | 92.8 | 99.7 | 35% Crystalline form A of shuangzuocaotong ·+ diflufenican SC | 78.8 | 65.2 | 70.3 |
| 40% Crystalline form C of shuangzuocaotong + picolinafen SC | 18.0 | 94.7 | 97.3 | 40% Crystalline form A of shuangzuocaotong ·+ picolinafen SC | 18.0 | 67.9 | 70.4 |
| 12% Crystalline form C of shuangzuocaotong ·+ flufenacet SC | 67.5 | 89.5 | 97.4 | 12% Crystalline form A of shuangzuocaotong ·+ flufenacet SC | 67.5 | 55.4 | 46.8 |
| 22% Crystalline form C of shuangzuocaotong ·+ MCPA-dimethylamine salt SC | 99.0 | 84.6 | 96.3 | 22% Crystalline form A of shuangzuocaotong ·+ MCPA-dimethylamine salt SC | 99.0 | 58.2 | 64.1 |
| 50% Crystalline form C of shuangzuocaotong ·+ chlortoluron WP | 375.0 | 86.9 | 94.6 | 50% Crystalline form A of shuangzuocaotong ·+ chlortoluron WP | 375.0 | 57.4 | 60.3 |
| 33% Crystalline form | 123.8 | 85.3 | 94.1 | 33% Crystalline form | 123.8 | 52.8 | 65.4 |

TABLE 2-continued

Control effect (%) of preparations with different crystalline forms of shuangzuocaotong (30 DAA).

| Preparation | Application rate g/hm² | Barnyard-grass control effect % | Crickweed | Preparation | Application rate g/hm² | Barnyard-grass control effect % | Crickweed |
|---|---|---|---|---|---|---|---|
| C of shuangzuocaotong + prometryn WP | | | | A of shuangzuocaotong + prometryn WP | | | |
| 3% Crystalline form C of shuangzuocaotong + carfentrazone-ethyl WDG | 13.5 | 82.2 | 93.2 | 3% Crystalline form A of shuangzuocaotong + carfentrazone-ethyl WDG | 13.5 | 50.6 | 72.9 |
| 14% Crystalline form C of shuangzuocaotong + metribuzin WDG | 63.0 | 97.3 | 97.2 | 14% Crystalline form A of shuangzuocaotong + metribuzin WDG | 63.0 | 50.5 | 65.2 |
| 3% Crystalline form C of shuangzuocaotong + fluoroglycofen-ethyl EC | 13.5 | 95.3 | 96.2 | 3% Crystalline form A of shuangzuocaotong + fluoroglycofen-ethyl EC | 13.5 | 55.9 | 70.3 |
| 9% Crystalline form C of shuangzuocaotong + fenoxaprop-P-ethyl EW | 54.0 | 97.1 | 85.3 | 9% Crystalline form A of shuangzuocaotong + fenoxaprop-P-ethyl EW | 54.0 | 55.6 | 51.3 |
| 14% Crystalline form C of shuangzuocaotong + clodinafop-propargyl EW | 52.5 | 94.2 | 84.3 | 14% Crystalline form A of shuangzuocaotong + clodinafop-propargyl EW | 52.5 | 63.8 | 55.6 |
| 17% Crystalline form C of shuangzuocaotong + pinoxaden EW | 51.0 | 94.9 | 86.2 | 17% Crystalline form A of shuangzuocaotong + pinoxaden EW | 51.0 | 63.6 | 52.7 |
| 65% Crystalline form C of shuangzuocaotong + tralkoxydim WDG | 195.0 | 93.7 | 87.4 | 65% Crystalline form A of shuangzuocaotong + tralkoxydim WDG | 195.0 | 62.1 | 50.6 |
| 39% Crystalline form C of shuangzuocaotong + halosulfuron-methyl WDG | 29.3 | 96.2 | 95.2 | 39% Crystalline form A of shuangzuocaotong + halosulfuron-methyl WDG | 29.3 | 52.3 | 67.8 |
| 7% Crystalline form C of shuangzuocaotong + mesosulfuron-methyl OD | 15.1 | 95.9 | 96.4 | 7% Crystalline form A of shuangzuocaotong + mesosulfuron-methyl OD | 15.1 | 50.2 | 73.5 |
| 11% Crystalline form C of shuangzuocaotong + flucarbazone-sodium OD | 24.8 | 94.2 | 96.8 | 11% Crystalline form A of shuangzuocaotong + flucarbazone-sodium OD | 24.8 | 65.3 | 62.9 |
| 6% Crystalline form C of shuangzuocaotong + florasulam OD | 13.5 | 82.1 | 98.2 | 6% Crystalline form A of shuangzuocaotong + florasulam OD | 13.5 | 59.6 | 51.3 |
| 7% Crystalline form C of shuangzuocaotong + pyroxsulam OD | 15.8 | 95.2 | 99.3 | 7% Crystalline form A of shuangzuocaotong + pyroxsulam OD | 15.8 | 50.7 | 72.6 |
| 38% Crystalline form C of shuangzuocaotong + bentazone OD | 285.0 | 84.3 | 100.0 | 38% Crystalline form A of shuangzuocaotong + bentazone OD | 285.0 | 52.4 | 70.5 |

The above examples give description to the basic principles, main characteristics and advantages of the present invention. It should be understood by those skilled in the art that the present invention is not limited to the above examples. The aforementioned examples and the descriptions in the specification is only for explanation of the present invention. Changes and modifications can be made for the present invention within the range of the principles of the present invention. All these changes and modifications are in the protection scope of the present invention.

The invention claimed is:

1. Crystalline form C of shuangzuocaotong, characterized in that the Crystalline form C has an X-ray powder diffraction pattern having characteristic absorption peaks at the following 2θ positions: 10.159, 10.658, 13.318, 14.579, 16.096, 18.061, 19.322, 19.68, 20.04, 20.659, 21.281, 23, 24.16, 24.619, 26.101, 26.74, 30.359, 31.018, 32.378, 35.398 and 38.26 degrees, wherein the 2θ has an error range within ±0.2°.

2. The Crystalline form C of shuangzuocaotong according to claim 1, characterized in that the characteristic absorption peaks have the following Ho values: 22, 22.9, 18.9, 28.7, 100, 21.5, 17.6, 35, 10.7, 18.3, 11.1, 55.4, 61.3, 28.1, 12.2, 7.6, 10.1, 6.1, 9.4, 8.2 and 7.6, respectively.

Figure 2:
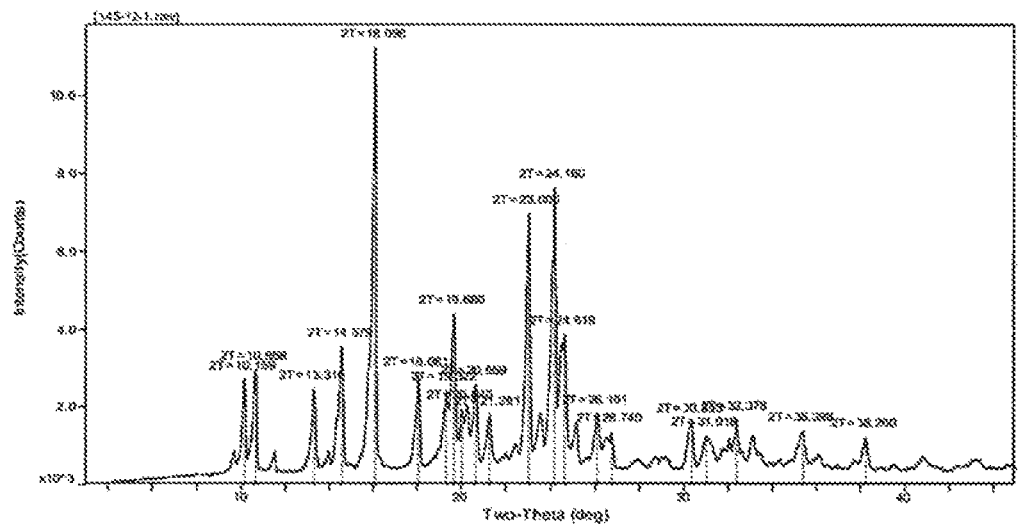
FIG. 2 is the XRPD pattern of Crystalline form C of shuangzuocaotong in Example 2 of the present invention.

3. The Crystalline form C of shuangzuocaotong according to claim 1, characterized in that the X-ray powder diffraction pattern is basically the same as shown in FIG. 2.

4. A method for preparing the Crystalline form C of shuangzuocaotong according to claim 1, comprising the following steps: shuangzuocaotong is dissolved in a solvent which is selected from a group consisting of: absolute ethyl alcohol, n-propyl alcohol, isobutyl alcohol, absolute ethyl ether, methyl tertiary butyl ether, butyl acetate, methyl benzene and isopropyl benzene, and then heated to complete dissolution; the solvent is removed by natural volatilization, and the Crystalline form C is obtained.

5. A herbicidal compounded composition, comprising the Crystalline form C of shuangzuocaotong according to claim 1 and an adjuvant.

6. The herbicidal compounded composition according to claim 5, wherein the composition further comprises additional active ingredients.

7. The herbicidal compounded composition according to claim 6, wherein the composition has a total mass content of active ingredients within 75%.

8. The herbicidal compounded composition according claim 5, wherein the composition has a formulation selected from a group consisting of: suspension concentrate, oil dispersion, emulsifiable concentrate, microemulsion, granule, suspoemulsion or water-dispersible granule.

9. A method for controlling broadleaf weeds or some gramineous weeds in wheat, the method comprising a step of administrating the Crystalline form C of shuangzuocaotong according to claim 1 or the herbicidal compounded composition comprising the Crystalline form C of shuangzuocaotong according to claim 1 to the broadleaf weeds or gramineous weeds.

10. The herbicidal compounded composition according to claim 5, wherein the adjuvant is one or more selected from a group consisting of: solvents, solid diluents, emulsifiers, humectants, dispersants, antifreezes, defoamers and thickeners.

11. The herbicidal compounded composition according to claim 6, wherein the active ingredient is selected from a group consisting of: MCPA-Na, MCPA-isooctyl ester, 2,4-D butyl ester, 2,4-D isooctyl ester, MCPA-dimethylamine salt, fluroxypyr, fluroxypyr-mepthyl, halauxifen-methyl, dicamba, isoproturon, chlorotoluron, diflufenican, picolinafen, carfentrazone-ethyl, fluoroglycofen-ethyl, fenoxaprop-P-ethyl, clodinafop-propargyl (acid), tralkoxydim, pinoxaden, halosulfuron-methyl, mesosulfuron-methyl, flucarbazone-sodium, florasulam, pyroxsulam, metribuzin, prometryn, terbutryn, bentazone, bromoxynil, bromoxynil octanoate, flufenacet and any combination thereof.

12. The herbicidal compounded composition according to claim 6, wherein the composition has a total mass content of active ingredients within 50%.

\* \* \* \* \*